(12) United States Patent
Berthelon et al.

(10) Patent No.: US 6,265,437 B1
(45) Date of Patent: Jul. 24, 2001

(54) AMINOALKANESULPHONIC ACID DERIVATIVES, THEIR PREPARATION AND THEIR USE AS MEDICAMENTS

(75) Inventors: Jean-Jacques Berthelon, Lyons; Philippe Durbin, Villeurbanne, both of (FR)

(73) Assignee: LIPHA, Lyons (FR)

( * ) Notice: Subject to any disclaimer, the term of this patent is extended or adjusted under 35 U.S.C. 154(b) by 0 days.

(21) Appl. No.: 09/601,079

(22) PCT Filed: Jan. 27, 1998

(86) PCT No.: PCT/FR98/00147

§ 371 Date: Oct. 12, 2000

§ 102(e) Date: Oct. 12, 2000

(87) PCT Pub. No.: WO99/37606

PCT Pub. Date: Jul. 29, 1999

(51) Int. Cl.[7] ............ A61K 31/185; C07C 309/15; C07C 309/24
(52) U.S. Cl. .................... 514/474; 514/576; 514/578; 556/120; 562/44; 562/105
(58) Field of Search .................... 514/494, 576, 514/578; 556/120; 562/44, 105

(56) References Cited

U.S. PATENT DOCUMENTS 4,199,601 * 4/1980 Durlach .................. 514/578
4,355,043 * 10/1982 Durlach .................. 514/494

FOREIGN PATENT DOCUMENTS

2457281 * 12/1980 (FR) .

* cited by examiner

Primary Examiner—Fiona T. Powers
(74) Attorney, Agent, or Firm—Young & Thompson

(57) ABSTRACT

Derivatives of sulphonic aminoalkane acids, corresponding to formula (I)
where X is

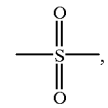

$R_1$, $R_2$ and $R_3$ are selected from hydrogen and a $C_1$–$C_7$ alkyl radical, and A is a group of the formula (e) where v and w are 0, 1, 2 or a group of formula (f) where $R_5$ and $R_6$ are selected independently of each other from hydrogen, a $C_1$–$C_7$ alkyl radical, an aryl radical having between 6 and 14 carbon atoms and a heteroaryl radical; t is 1–3; $R_4$ is selected from hydrogen, a $C_1$–$C_7$ alkyl radical, a $CF_3$ radical, an aryl radical having between 6 and 14 carbon atoms and a heteroaryl radical; M is a monovalent metal (Na, K, Li) or a divalent metal (Ca, Mg, Sr, Zn); m is 1 or 2; p is 1–2 and q is 1–2; and where p and q are such that the electrical neutrality of the salt is ensured. The compounds can be used for the treatment of alcohol dependence.

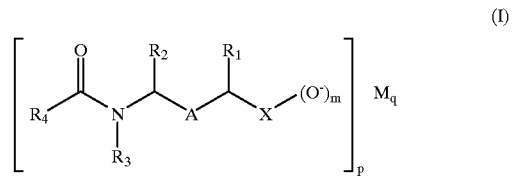

(I)

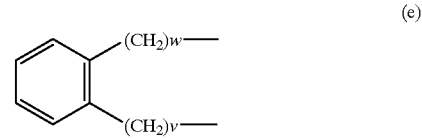

(e)

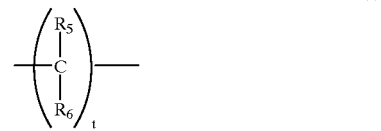

(f)

5 Claims, 1 Drawing Sheet

AMINOALKANESULPHONIC ACID DERIVATIVES, THEIR PREPARATION AND THEIR USE AS MEDICAMENTS

The present invention relates to sulphonic, phosphonic and phosphinic acid derivatives intended for the treatment of dependency on alcohol and on other substances.

Japanese Patent JP 7612093 discloses compounds of formula:

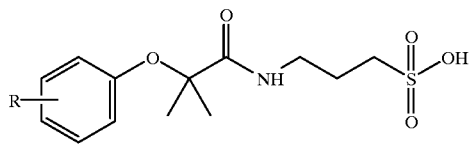

as hypocholesterolaemics

Japanese Patent JP 63201643 discloses the use of potassium 4-palmitylsulphonate as adjuvant in photographic substrates.

FR-A-2,457,281 has disclosed acetylhomotaurine salts as membrane stabilizers. The calcium salt of acethylhomotaurine is used in the treatment of alcoholism (under the name of acamprosate).

A subject-matter of the present invention is novel sulphonic, phosphonic and phosphinic acid derivatives represented by the formula (I):

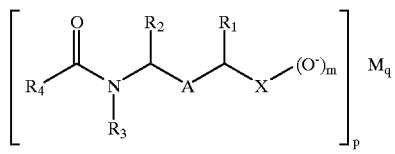

in which
X is

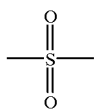

$R_1$, $R_2$ and $R_3$ are selected from hydrogen and a $C_1$–$C_7$ alkyl radical,
A is a group of formula

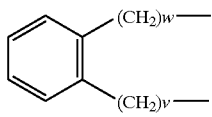

with v and w=0, 1 or 2
or a group of formula

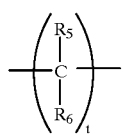

$R_5$ and $R_6$ being selected, independently of one another, from hydrogen, a $C_1$–$C_7$ alkyl radical, an aryl radical having from 6 to 14 carbon atoms and a heteroaryl radical selected from furyl, thienyl and thiazolyl, it being possible for the aryl and heteroaryl radicals to carry 1 to 3 substituents selected from a $C_1$–$C_7$ alkyl group, a halogen or a trifluoromethyl group, and t=1–3, $R_4$ is selected from hydrogen, a $C_1$–$C_7$ alkyl radical, a $CF_3$ radical, an aryl radical having from 6 to 14 carbon atoms and a heteroaryl radical selected from furyl, thienyl and thiazolyl, it being possible for the aryl and heteroaryl radicals to carry 1 to 3 substituents selected from a $C_1$–$C_7$ alkyl group, a halogen or a trifluoromethyl group, M is a monovalent metal (Na, K, Li) or a divalent metal (Ca, Mg, Sr, Zn), m=1 or 2, p=1–2 and q=1–2, p and q being such that the electrical neutrality of the salt is ensured, $R_4$ not being a methyl radical when $R_1$, $R_2$ and $R_3$ are hydrogen.

The compounds of the invention can comprise chiral centres. The optical isomers, the racemates, the enantiomers and the diastereoisomers form part of the invention.

The Applicant company has shown that this family of products make it possible to decrease the consumption of alcohol in rats exhibiting alcohol dependency. Their therapeutic applications relate, inter alia, to the field of dependency on alcohol and on other substances capable of leading to habituation, such as, for example, opiates, nicotine derivatives, caffeine derivatives, amphetamines, cannabinoids or tranquillizers.

The present invention also applies to pharmaceutical compositions comprising, as active principle, one of the compounds of formula (I), optionally in combination with one or more pharmaceutically acceptable excipients or vehicles.

Mention may be made, among the compositions according to the invention, by way of example and without implied limitation, of tablets, capsules, including hard gelatin capsules, or solutions to be taken orally.

The compounds of the invention can be administered at doses of between 0.01 g and 1 g from one to three times daily.

Mention may be made, among the preferred compounds of the formula 1, of, for example:

calcium 3-(2-(methyl)propanoylamino)propanesulphonate
magnesium 3-(2-(methyl)propanoylamino)propanesulphonate
calcium 3-(butanoylamino)propanesulphonate
magnesium 3-(butanoylamino)propanesulphonate
calcium 3-(pentanoylamino)propanesulphonate
calcium 3-(benzoylamino)propanesulphonate
magnesium 3-(benzoylamino)propanesulphonate
zinc 3-(2-(methyl)propanoylamino)propanesulphonate
strontium 3-(2-(methyl)propanoylamino)propanesulphonate
calcium 3-(3-(methyl)butanoylamino)propanesulphonate
magnesium 3-(3-(methyl)butanoylamino)propanesulphonate
calcium 3-(2-2-(dimethyl)propanoylamino)propanesulphonate
magnesium 3-(2-2-(dimethyl)propanoylamino)propanesulphonate
calcium 3-(acetylamino)-2-methylpropanesulphonate
calcium 3-(acetylamino)-3-methylpropanesulphonate
magnesium 3-(acetylamino)-3-methylpropanesulphonate calcium 3-(acetylamino)-1-methylpropanesulphonate
calcium 3-(acetylamino)-2-phenylpropanesulphonate
calcium 2-(2-acetylaminomethyl)phenylmethanesulphonate
calcium N-methyl-3-(acetylamino)propanesulphonate
calcium 3-(acetylamino)-2-2-dimethylpropanesulphonate
calcium 3-(trifluoromethylcarbonyl)propanesulphonate Preference is very particularly given to the compounds of formula I in which $R_4$ is a $C_2$–$C_7$ alkyl radical and in particular a branched radical.

The following compounds also form part of the invention:

3-((2-methyl)propanoylamino)propanesulphonic acid
3-(butanoylamino)propanesulphonic acid
3-(pentanoylamino)propanesulphonic acid
3-(benzoylamino)propanesulphonic acid
3-(acetylamino)propanephosphonic acid
N-methyl-3-(acetylamino)propanesulphonic acid
3-((3-methyl)butanoylamino)propanesulphonic acid
3-((2-2-dimethyl)propanoylamino)propanesulphonic acid
3-(acetylamino)-2-methylpropanesulphonic acid
3-(acetylamino)-3-methylpropanesulphonic acid
3-(acetylamino)-1-methylpropanesulphonic acid
3-(acetylamino)-2-phenylpropanesulphonic acid
2-(2-acetylaminomethyl)phenylmethanesulphonic acid
3-(acetylamino)-2-2-dimethylpropanesulphonic acid
3-(trifluoromethylcarbonoyl)propanesulphonic acid The invention is also targeted at a process for the preparation of the compounds of the invention. The latter is summarized in Scheme 1.

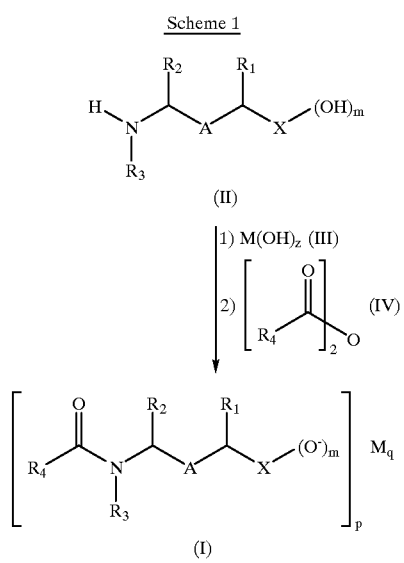

The reaction can be carried out by reacting the compound of formula (II) with the base $M(OH)_z$, where z is the valency of M, and then, while maintaining at a temperature of between 15° C. and 20° C., the anhydride of formula (IV) is added. Reaction is allowed to take place overnight and, after treatment, the compound of formula (I) is obtained.

The list of the following examples illustrating the invention is not limiting. In the proton nuclear magnetic resonance ($^1$H NMR) data, the following abbreviations were employed:
ppm for parts per million
s for singlet
d for doublet
t for triplet
q for quartet
m for complex unresolved peak
j for the couplings, expressed in Hertz
dd for double doublet

EXAMPLE 1 calcium 3-(2-2-(dimethyl)propanoylamino)propanesulphonate

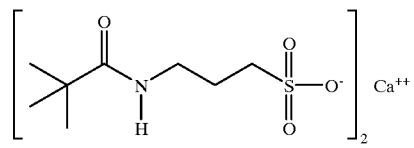

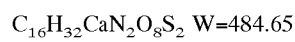

8.1 g (0.11 mol) of $Ca(OH)_2$ are added to a solution of 22.3 g (0.1 mol) of aminopropanesulphonic acid in a sufficient amount of distilled water. A white suspension is obtained, which suspension is kept stirred for 15 minutes.

The suspension is cooled to 15° C. and 35.2 g (0.2 mol) of (2-2-dimethyl)propanoic anhydride are added dropwise while maintaining the temperature between 15° C. and 20° C. The mixture is subsequently brought to room temperature overnight with stirring. The solution obtained is subsequently evaporated under vacuum and the residue is taken up with q.s. of distilled water to dissolve it. 17.6 g (0.1 mol) of (2-2-dimethyl)propanoic anhydride are again added between 15° C. and 20° C. and then the reaction mixture is again left overnight with stirring at room temperature. The mixture is evaporated to dryness under vacuum. The residue is taken up in 300 ml of absolute ethanol comprising 1.5 ml of concentrated hydrochloric acid. The precipitate obtained is filtered off and dried. It is subsequently taken up in the amount of distilled water necessary to dissolve it. After washing with ether, acetone is slowly added to the aqueous phase until a persistent cloudiness is obtained. Stirring is continued until precipitation is complete, and the product is filtered off and dried.

Weight obtained: 4.5 g (Yd: 37%)

$MP_G$: 300° C.

$IR_{\gamma C=O}$: 1623 cm$^{-1}$ $^1$H NMR ($D_2O$) δ in ppm: 0.83 (s, 3CH$_3$), 1.59 (m, CH$_2$), 2.56 (m, CH$_2$), 2.97 (m, CH$_2$).

Analysis by weight: ($C_{16}H_{32}CaN_2O_8S_3.0.25H_2O$)

|  | C % | H % | Ca % | N % | S % |
| --- | --- | --- | --- | --- | --- |
| Calculated | 39.65 | 6.66 | 8.27 | 5.78 | 13.23 |
| Found | 38.72 | 6.61 | 8.49 | 5.87 | 13.33 |

EXAMPLE 2 calcium 3-(2-(methyl)propanoylamino)propanesulphonate

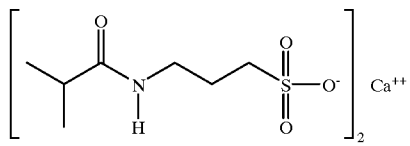

$C_{14}H_{28}CaN_2O_8S_2$ MW=456.60

$MP_G$>360° C.

$IR_{\gamma C=O}$: 1644 cm$^{-1}$ $^1$H NMR (D$_2$O) δ in ppm: 1.1 (d, 2CH$_3$), 1.93 (m, CH$_2$), 2.48 (m, CH$_2$), 2.90 (m, CH$_2$), 3.29 (t, CH$_2$)

Analysis by weight:

|  | C % | H % | Ca % | N % | S % |
|---|---|---|---|---|---|
| Calculated | 36.83 | 6.18 | 8.78 | 6.14 | 14.04 |
| Found | 36.96 | 6.27 | 8.70 | 6.27 | 14.25 |

EXAMPLE 3 magnesium 3-(2-(methyl)propanoylamino)propanesulphonate

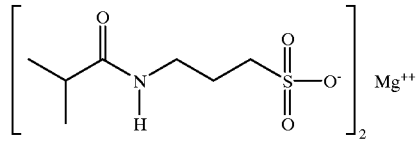

$C_{14}H_{28}MgN_2O_8S_2$ MW=440.83

$MP_G$: 270–273° C.

$IR_{\gamma C=O}$: 1644 cm$^{-1}$ $^1$H NMR (D$_2$O) δ in ppm: 0.95 (d, 2CH$_3$), 1.78 (m, CH$_2$), 2.34 (m, CH$_2$), 2.76 (m, CH$_2$), 3.14 (t, CH$_2$)

Analysis by weight:

|  | C % | H % | Mg % | N % | S % |
|---|---|---|---|---|---|
| Calculated | 36.65 | 6.59 | 5.30 | 6.11 | 13.97 |
| Found | 36.56 | 6.60 | 5.52 | 6.15 | 13.57 |

EXAMPLE 4 calcium 3-(butanoylamino)propanesulphonate

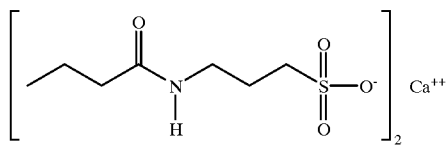

$C_{14}H_{28}CaN_2O_8S_2$ MW=456.60

$MP_G$>360° C.

$IR_{\gamma C=O}$: 1633 cm$^{-1}$ $^1$H NMR (D$_2$O) δ in ppm: 0.81 (t, CH$_3$), 1.49 (m, CH$_2$), 1.84 (m, CH$_2$), 2.12 (t, CH$_2$), 2.83 (m, CH$_2$), 3.21 (t, CH$_2$)

Analysis by weight:

|  | C % | H % | Ca % | N % | S % |
|---|---|---|---|---|---|
| Calculated | 36.83 | 6.18 | 8.78 | 6.14 | 14.04 |
| Found | 36.84 | 6.23 | 8.79 | 6.30 | 14.29 |

EXAMPLE 5 magnesium 3-(butanoylamino)propanesulphonate

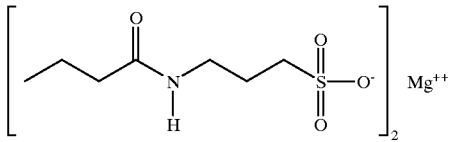

$C_{14}H_{28}MgN_2O_8S_2$ MW=440.83

$MP_G$: 325° C.

$IR_{\gamma C=O}$: 1635 cm$^{-1}$ $^1$H NMR (D$_2$O) δ in ppm: 0.94 (t, CH$_3$), 1.64 (m, CH$_2$), 1.98 (m, CH$_2$), 2.26 (t, CH$_2$), 2.97 (m, CH$_2$), 3.35 (t, CH$_2$)

Analysis by weight: ($C_{14}H_{28}MgN_2O_8S_2.2H_2O$)

|  | C % | H % | Mg % | N % | S % |
|---|---|---|---|---|---|
| Calculated | 35.26 | 6.76 | 5.10 | 5.38 | 13.45 |
| Found | 35.11 | 6.62 | 5.35 | 5.90 | 13.10 |

EXAMPLE 6 calcium 5-(acetylamino)pentanesulphonate

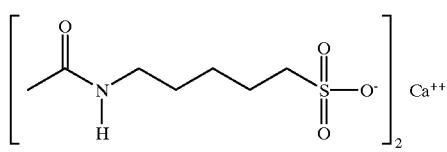

$C_{14}H_{28}CaN_2O_8S_2$ MW=456.60

$MP_G$: 325–330° C.

$IR_{\gamma C=O}$: 1637 cm$^{-1}$ $^1$H NMR (D$_2$O) δ in ppm: 1.38–1.58 (m, 2CH$_2$), 1.74 (m, CH$_2$), 1.97 (s, CH$_2$), 2.93 (t, CH$_2$), 3.17 (t, CH$_2$)

Analysis by weight:

|  | C % | H % | Ca % | N % | S % |
|---|---|---|---|---|---|
| Calculated | 36.83 | 6.18 | 8.78 | 6.14 | 14.04 |
| Found | 36.53 | 6.25 | 8.44 | 6.29 | 13.95 |

EXAMPLE 7 calcium 3-(pentanoylamino)propanesulphonate

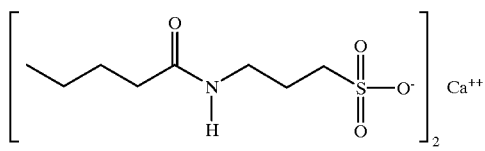

$C_{16}H_{32}CaN_2O_8S_2$ MW=484.65

$MP_G$>360° C.

$IR_{\gamma C=O}$: 1633 cm$^{-1}$ $^1$H NMR (D$_2$O) δ in ppm: 0.99 (t, CH$_3$), 1.4 (m, CH$_2$), 1.67 (m, CH$_2$), $_{2.04}$ (m, CH$_2$), 2.35 (t, CH$_2$), 3.03 (m, CH$_2$), 3.41 (t, CH$_2$)

Analysis by weight:

|  | C % | H % | Ca % | N % | S % |
|---|---|---|---|---|---|
| Calculated | 39.65 | 6.66 | 8.27 | 5.78 | 13.23 |
| Found | 39.75 | 6.75 | 8.33 | 5.54 | 13.23 |

EXAMPLE 8 calcium 3-(benzoylamino)propanesulphonate

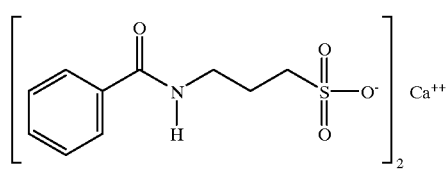

$C_{20}H_{24}CaN_2O_8S_2$ MW=524.63

$MP_G$>360° C.

$IR_{\gamma C=O}$: 1637 cm$^{-1}$ $^1$H NMR (D$_2$O) δ in ppm: 1.78 (m, CH$_2$), 2.72 (m, CH$_2$), 3.21 (t, CH$_2$), 7.2–7.45 (m, 5AR)

Analysis by weight: ($C_{20}H_{24}CaN_2O_8S_2 \cdot 1H_2O$)

|  | C % | H % | Ca % | N % | S % |
|---|---|---|---|---|---|
| Calculated | 44.27 | 4.83 | 7.39 | 5.16 | 11.82 |
| Found | 43.98 | 4.75 | 7.23 | 5.11 | 11.42 |

EXAMPLE 9 magnesium 3-(benzoylamino)propanesulphonate

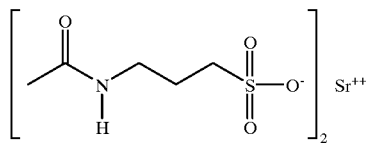

$C_{20}H_{24}MgN_2O_8S_2$ MW=508.86

$MP_G$: 350° C.

$IR_{\gamma C=O}$: 1640 cm$^{-1}$ $^1$H NMR (D$_2$O) δ in ppm: 1.9 (m, CH$_2$), 2.83 (m, CH$_2$), 3.33 (t, CH$_2$), 7.32–7.68 (m, 5AR)

Analysis by weight: ($C_{20}H_{24}MgN_2O_8S_2 \cdot 2H_2O$)

|  | C % | H % | Mg % | N % | S % |
|---|---|---|---|---|---|
| Calculated | 44.08 | 5.18 | 4.46 | 5.14 | 11.77 |
| Found | 44.49 | 5.18 | 4.48 | 5.16 | 11.42 |

EXAMPLE 10 strontium 3-(acetylamino)propanesulphonate $C_{10}H_{20}N_2O_8S_2Sr$ MW=448.03

$MP_G$: 305–308° C.

$IR_{\gamma C=O}$: 1632 cm$^{-1}$ $^1$H NMR (D$_2$O) δ in ppm: 1.6 (m, CH$_2$), 1.66 (s, CH$_3$), 2.61 (m, CH$_2$), 2.97 (t, CH$_2$)

Analysis by weight:

|  | C % | H % | N % | S % | Sr % |
|---|---|---|---|---|---|
| Calculated | 26.81 | 4.50 | 6.25 | 14.31 | 19.56 |
| Found | 20.77 | 4.57 | 6.16 | 13.77 | 19.53 |

EXAMPLE 11 zinc 3-(2-(methyl)propanylamino)propanesulphonate

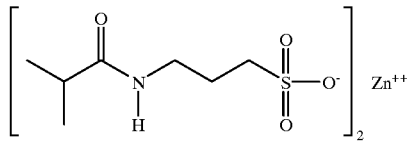

$C_{14}H_{28}N_2O_8S_2Zn$ MW=481.89

$MP_G$: 114° C.

$IR_{\gamma C=O}$: 1637 cm$^{-1}$ $^1$H NMR (D$_2$O) δ in ppm: 0.77 (d, CH$_3$), 1.6 (m, CH$_2$), 2.17 (m, CH), 2.58 (m, CH$_2$), 2.97 (t, CH$_2$)

Analysis by weight: ($C_{14}H_{28}N_2O_8S_2Zn.2H_2O$)

|            | C %   | H %  | N %  | S %   | Zn %  |
|------------|-------|------|------|-------|-------|
| Calculated | 32.46 | 6.27 | 5.41 | 12.38 | 12.62 |
| Found      | 32.46 | 6.27 | 5.30 | 12.38 | 12.44 |

EXAMPLE 12 strontium 3-(2-(methyl)propanoylamino)propanesulphonate

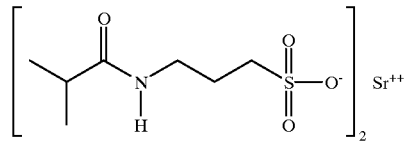

$C_{14}H_{28}N_2O_8S_2Sr$ MW=504.14

$MP_G$: 345–350° C.

$IR_{\gamma C=O}$: 1642 cm$^{-1}$ $^1$H NMR (D$_2$O) δ in ppm: 1 (d, CH$_3$), 1.83 (m, CH$_2$), 2.39 (m, CH), 2.8 (m, CH$_2$), 3.19 (t, CH$_2$)

Analysis by weight:

|            | C %   | H %  | N %  | S %   | Sr %  |
|------------|-------|------|------|-------|-------|
| Calculated | 33.36 | 5.60 | 5.56 | 12.72 | 17.38 |
| Found      | 33.12 | 5.62 | 5.24 | 12.24 | 17.85 |

EXAMPLE 13 calcium 3-(3-(methyl)butanoylamino)propanesulphonate

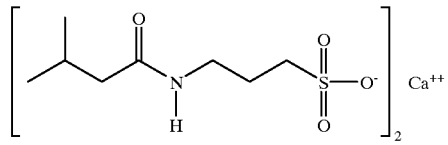

$C_{16}H_{32}CaN_2O_8S_2$ MW=484.65

$MP_G$>350° C.

$IR_{\gamma C=O}$: 1633 cm$^{-1}$ $^1$H NMR (D$_2$O) δ in ppm: 0.91 (d, 2CH$_3$), 1.89–2.12 (m, 2CH$_2$+CH), 2.92 (m, CH$_2$), 3.3 (t, CH$_2$)

Analysis by weight:

|            | C %   | H %  | Ca % | N %  | S %   |
|------------|-------|------|------|------|-------|
| Calculated | 39.65 | 6.66 | 8.27 | 5.78 | 13.23 |
| Found      | 39.07 | 6.41 | 8.37 | 5.83 | 13.08 |

EXAMPLE 14 magnesium 3-(3-(methyl)butanoylamino)propanesulphonate

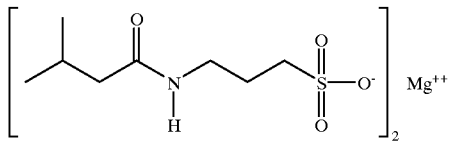

$C_{16}H_{32}MgN_2O_8S_2$ MW=468.88

$MP_G$: 280–287° C.

$IR_{\gamma C=O}$: 1644 cm$^{-1}$ $^1$H NMR (D$_2$O) δ in ppm: 0.66 (d, 2CH$_3$), 1.63–1.87 (m, 2CH$_2$+CH), 2.67 (m, CH$_2$), 3.05 (t, CH$_2$)

Analysis by weight: ($C_{16}H_{32}MgN_2O_8S_2.2H_2O$)

|            | C %   | H %  | Mg % | N %  | S %   |
|------------|-------|------|------|------|-------|
| Calculated | 38.05 | 7.18 | 4.81 | 5.55 | 12.70 |
| Found      | 38.40 | 7.10 | 5.53 | 5.67 | 13.13 |

EXAMPLE 15 magnesium 3-(2,2-(dimethyl)propanoylamino)
propanesulphonate

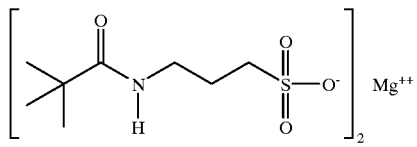

$C_{16}H_{32}MgN_2O_8S_2$ MW=468.88

$MP_G$: 200–250° C.

$IR_{\gamma C=O}$: 1630 cm$^{-1}$ $^1$H NMR (D$_2$O) δ in ppm: 1.28 (s, 3CH$_3$), 2.04 (m, CH$_2$), 3.02 (m, CH$_2$), 3.42 (t, CH$_2$)

Analysis by weight: (C$_{16}$H$_{32}$MgN$_2$O$_8$S$_2$.5H$_2$O)

|  | C % | H % | Mg % | N % | S % |
|---|---|---|---|---|---|
| Calculated | 34.42 | 7.57 | 4.35 | 5.04 | 11.49 |
| Found | 33.94 | 7.48 | 4.35 | 5.38 | 11.68 |

EXAMPLE 16 calcium 3-(acetylamino)-2-
methylpropanesulphonate

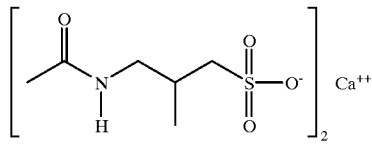

$C_{12}H_{24}CaN_2O_8S_2$ MW=428.54

$MP_G$: 270° C.

$IR_{\gamma C=O}$: 1638 cm$^{-1}$ $^1$H NMR (D$_2$O) δ in ppm: 1.15 (d, CH$_3$), 2.07 (s, CH$_3$), 2.25 (m, CH), 2.83 (m, CH), 3.02 (m, CH), 3.24 (n, CH$_2$)

Analysis by weight: (C$_{12}$H$_{24}$CaN$_2$O$_8$S$_2$.0.5H$_2$O)

|  | C % | H % | Ca % | N % | S % |
|---|---|---|---|---|---|
| Calculated | 33.63 | 5.65 | 9.35 | 6.54 | 14.96 |
| Found | 32.41 | 5.74 | 9.28 | 6.27 | 14.47 |

EXAMPLE 17 calcium 3-(acetylamino)-3-
methylpropanesulphonate

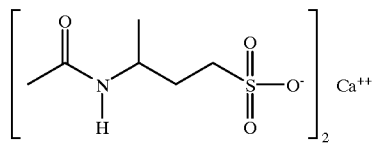

$C_{12}H_{24}CaN_2O_8S_2$ MW=428.54

$MP_G$: 275–285° C.

$IR_{\gamma C=O}$: 1364 cm$^{-1}$ $^1$H NMR (D$_2$O) δ in ppm: 1.15 (d, CH$_3$), 1.85 (m, CH$_2$), 1.98 (s, CH$_2$), 2.91 (t, CH$_2$), 3.94 (m, CH)

Analysis by weight: (C$_{12}$H$_{24}$CaN$_2$O$_8$S$_2$.0.5H$_2$O)

|  | C % | H % | Ca % | N % | S % |
|---|---|---|---|---|---|
| Calculated | 32.96 | 5.76 | 9.17 | 6.41 | 14.66 |
| Found | 32.61 | 5.79 | 8.95 | 6.34 | 14.29 |

EXAMPLE 18 magnesium 3-(acetylamino)-3-
methylpropaneslphonate

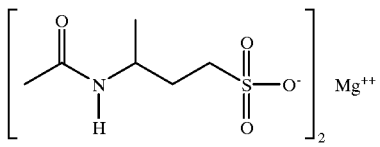

$C_{12}H_{24}CaN_2O_8S_2$ MW=428.54

$^1$H NMR (D$_2$O) δ in ppm: 1.1 (d, CH$_3$), 1.78 (m, CH$_2$), 1.9 (s, CH$_3$), 2.84 (t, CH$_2$), 3.85 (m, CH)

EXAMPLE 19 calcium 3-(acetylamino)-1-
methylpropanesulphonate

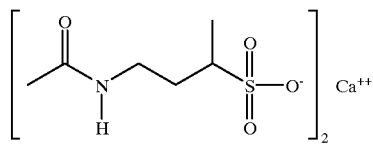

$C_{12}H_{24}CaN_2O_8S_2$ MW=428.54

$MP_G$>360° C.

$IR_{\gamma C=O}$: 1670 cm$^{-1}$ $^1$H NMR (D$_2$O) δ in ppm: 1.44 (d, CH$_3$), 1.77 (m, CH), 2.11 (s, CH$_3$), 2.33 (m, CH), 3.03 (m, CH), 3.45 (m, CH$_2$)

Analysis by weight:

|  | C % | H % | Ca % | N % | S % |
|---|---|---|---|---|---|
| Calculated | 33.63 | 5.65 | 9.35 | 6.54 | 14.96 |
| Found | 33.34 | 5.67 | 9.35 | 6.50 | 15.06 |

EXAMPLE 20 calcium 2-(2-acetylaminomethyl) phenylmethanesulphonate

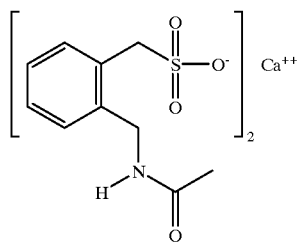

C$_{20}$H$_{24}$CaN$_2$O$_8$S$_2$ MW=524.63

MP$_G$: 260–265° C.

IR$_{\gamma C=O}$: 1640 cm$^{-1}$ $^1$H NMR (D$_2$O) δ in ppm: 2 (s, CH$_3$), 4.26 (m, CH$_2$), 7.3–7.4 (m, 4AR)

Analysis by weight: (C$_{20}$H$_{24}$CaN$_2$O$_8$S$_2$.1H$_2$O)

|  | C % | H % | Ca % | N % | S % |
|---|---|---|---|---|---|
| Calculated | 44.26 | 4.83 | 7.38 | 5.16 | 11.81 |
| Found | 44.45 | 4.80 | 7.63 | 5.23 | 11.25 |

EXAMPLE 21 calcium N-methyl-3-(acetylamino) propanesulphonate

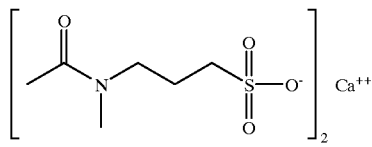

C$_{12}$H$_{24}$CaN$_2$O$_8$S$_2$ MW=428.54

IR$_{\gamma C=O}$: 1611 cm$^{-1}$ $^1$H NMR (D$_2$O) δ in ppm: 2 (m, CH$_2$), 2.1 (s, CH$_3$), 2.9 (m, CH$_2$), 3.06 (s, CH$_3$), 3.48 (n, CH$_2$)

EXAMPLE 23 calcium 3-(acetylamino)-2-phenylpropanesulphonate

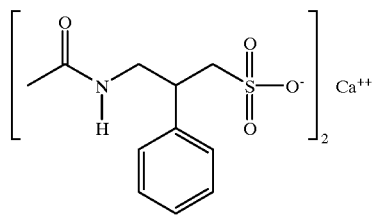

C$_{22}$H$_{28}$CaN$_2$O$_8$S$_2$ MW=552.69

MP$_G$: 240–250° C.

IR$_{\gamma C=O}$: 1636 cm$^{-1}$ $^1$H NMR (D$_2$O) δ in ppm: 1.88 (s, CH$_3$), 3.28–3.48 (m, 2CH$_2$), 3.59–3.66 (m, CH), 7.33–7.46 (m, 5Ar)

Analysis by weight: (C$_{22}$H$_{28}$CaN$_2$O$_8$S$_2$.1H$_2$O)

|  | C % | H % | Ca % | N % | S % |
|---|---|---|---|---|---|
| Calculated | 46.33 | 5.30 | 7.02 | 4.91 | 11.24 |
| Found | 46.66 | 5.04 | 7.23 | 4.96 | 10.36 |

The results of a pharmacological study on the compounds of the invention will be given below.

Consumption of Alcohol in Dependent Rats

Rats of the Long-Evans strain, weighing 200 g at the beginning of the test, are isolated in individual cages. In order to establish alcohol dependency, they are given, as the only drink, a 10% (V/V) solution of alcohol in water for 3 weeks. They are allowed to feed ad libitum.

At the end of this period of 3 weeks, the animal is offered the choice between water and aqueous/alcoholic solution for 2 weeks. Only the rats consuming more than 3 g/kg of alcohol per day are retained for the continuation of the tests.

On conclusion of this period, the product to be studied is administered intraperitoneally at a dose of 100 mg/kg/d for two weeks to batches of 5 to 8 rats. A control batch receives physiological water intra-peritoneally. All the rats have a free choice between water and the aqueous/alcoholic solution, and feeding is ad libitum.

The consumptions of water and of aqueous/alcohol solution are recorded before and during the treatment and are adjusted to the weight of the animal.

BRIEF DESCRIPTION OF THE DRAWINGS

The effect of the compound of Example 1 on the consumption of alcohol has been represented in FIG. 1 by the way of example.

In in vitro tests, it has furthermore been shown that these compounds have the ability to displace titiated calcium acetylhomotaurinate from a preparation of rat brain section.

Figure 1:
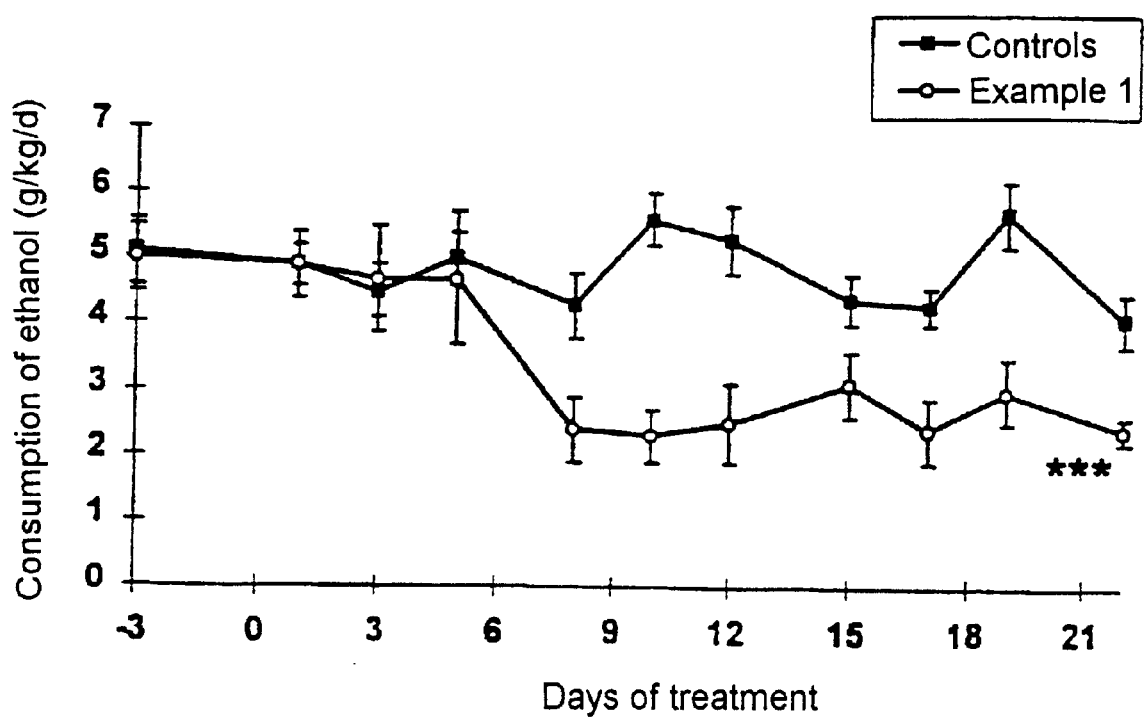

| Example | IC50 (μM) |
|---|---|
| 1 | 46.9 |
| 3 | 28.9 |

-continued

| Example | IC50 (μM) |
|---|---|
| 14 | 42 |
| 15 | 49.5 |
| 17 | 93 |

What is claimed is:
1. A compound selected from the compounds of formula

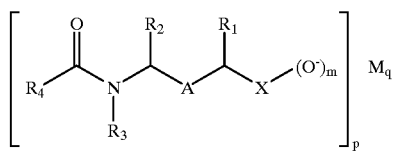

in which
X is

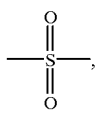

$R_1$, $R_2$ and $R_3$ are selected from hydrogen and a $C_1$–$C_7$ alkyl radical,
A is a group of formula

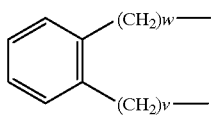

with v and w=0, 1 or 2
or a group of formula

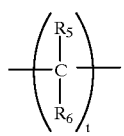

$R_5$ and $R_6$ being selected, independently of one another, from hydrogen, a $C_1$–$C_7$ alkyl radical, an aryl radical having from 6 to 14 carbon atoms and a heteroaryl radical selected from furyl, thienyl and thiazolyl, it being possible for the aryl and heteroaryl radicals to carry 1 to 3 substituents selected from a $C_1$–$C_7$ alkyl group, a halogen or a trifluoromethyl group, and t=1–3,
$R_4$ is selected from hydrogen, a $C_1$–$C_7$ alkyl radical, a $CF_3$ radical, an aryl radical having from 6 to 14 carbon atoms and a heteroaryl radical selected from furyl, thienyl and thiazolyl, it being possible for the aryl and heteroaryl radicals to carry 1 to 3 sustituents selected from a $C_1$–$C_7$ alkyl group, a halogen or a trifluoromethyl group,
M is a monovalent metal or a divalent metal,
m=1 or 2,
p=1–2 and q=1–2, p and q being such that the electrical neutrality of the salt is ensured,
$R_4$ not being a methyl radical when $R_1$, $R_2$ and $R_3$ are hydrogen.

2. A compound according to claim 1, selected from the following compounds:

calcium 3-(2-(methyl)propanoylamino)propanesulphonate
magnesium 3-(2-(methyl)propanoylamino)propanesulphonate
calcium 3-(butanoylamino)propanesulphonate
magnesium 3-(butanoylamino)propanesulphonate
calcium 3-(pentanoylamino)propanesulphonate
calcium 3-(benzoylamino)propanesulphonate
magnesium 3-(benzoylamino)propanesulphonate
zinc 3-(2-(methyl)propanoylamino)propanesulphonate
strontium 3-(2-(methyl)propanoylamino)propanesulphonate
calcium 3-(3-(methyl)butanoylamino)propanesulphonate
magnesium 3-(3-(methyl)butanoylamino)propanesulphonate
calcium 3-(2,2-(dimethyl)propanoylamino)propanesulphonate
magnesium 3-(2,2-(dimethyl)propanoylamino)propanesulphonate
calcium 3-(acetylamino)-2-methylpropanesulphonate
calcium 3-(acetylamino)-3-methylpropanesulphonate
magnesium 3-(acetylamino)-3-methylpropanesulphonate
calcium 3-(acetylamino)-1-methylpropanesulphonate
calcium 3-(acetylamino)-2-phenylpropanesulphonate
calcium 2-(acetylaminomethyl)phenylmethanesulphonate
calcium 3-(N-methyl-acetylamino)propanesulphonate
calcium 3-(acetylamino)-2,2-dimethylpropanesulphonate
calcium 3-(trifluoromethylcarbonyl)propanesulphonate.

3. Process for the preparation of a compound of formula I according to claim 1, which consists in reacting a compound of formula II:

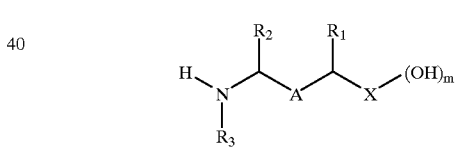

with a compound of formula III:

z being the valency of the metal M,
and then with a compound of formula IV:

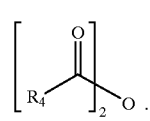

4. A pharmaceutical composition comprising a compound according to claim 1.
5. A pharmaceutical composition comprising a compound according to claim 2.

* * * * *